(12) United States Patent  (10) Patent No.: US 7,460,754 B2
Lee et al.  (45) Date of Patent: Dec. 2, 2008

(54) MEDICAL INSPECTION DEVICE

(75) Inventors: Kun-Feng Lee, Kaohsiung County (TW); Ching-Yi Wu, Taoyuan County (TW); Yu-Shih Chen, Taoyuan County (TW); Yuh-Jiuan Lin, Taipei County (TW); Hsi Feng Kao, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/688,771

(22) Filed: Mar. 20, 2007

(65) Prior Publication Data

US 2007/0237474 A1  Oct. 11, 2007

(30) Foreign Application Priority Data

Mar. 22, 2006  (TW) ............................. 95109856 A

(51) Int. Cl.
  *G02B 6/04* (2006.01)
(52) U.S. Cl. ...................... 385/115; 385/117; 385/119
(58) Field of Classification Search ................ 385/115, 385/119, 117
See application file for complete search history.

(56) References Cited

U.S. PATENT DOCUMENTS

| 3,884,222 | A | * | 5/1975 | Moore | 600/188 |
| 4,576,435 | A | * | 3/1986 | Nishioka | 385/119 |
| 4,915,626 | A | | 4/1990 | Lemmey | |
| 5,429,502 | A | | 7/1995 | Cooper et al. | |
| 5,496,307 | A | * | 3/1996 | Daikuzono | 606/15 |
| 5,833,683 | A | * | 11/1998 | Fuller et al. | 606/17 |
| 6,050,939 | A | | 4/2000 | Pak Wai | |
| 6,276,934 | B1 | * | 8/2001 | Rakocz | 433/29 |
| 2007/0225557 | A1 | * | 9/2007 | Lee et al. | 600/109 |

* cited by examiner

*Primary Examiner*—Ellen Kim
(74) *Attorney, Agent, or Firm*—Quintero Law Office

(57) ABSTRACT

A medical inspection device. A housing includes a transparent plate and a first opening. A reflective layer is formed in the housing and opposes the transparent plate. The first opening is between the reflective layer and the transparent plate. A grip is connected to the first opening and extends in the exterior of the housing. An optical fiber bundle is connected to the first opening and disposed in the grip. The optical fiber bundle extends to the exterior of the grip and outputs light into the housing. The light is output to the exterior of the housing by reflection of the reflective layer and through the transparent plate. An image outside the housing is received by the optical fiber bundle through the transparent plate and by reflection of the reflective layer.

4 Claims, 4 Drawing Sheets

MEDICAL INSPECTION DEVICE

BACKGROUND OF THE INVENTION

1. Field of the Invention

The invention relates to medical inspection, and in particular to a medical inspection device providing simplified structure and convenient operation.

2. Description of the Related Art

FIG. 1 is a schematic perspective view of a conventional laryngoscope 1. Conventionally, an operator (or a doctor) puts a spatula into a mouth cavity of a subject (or a patient) and inspects targets therein by reflection of a reflective mirror 11 of the laryngoscope 1. The nasopharynx and larynx of the subject are thus observed. Then, the operator (doctor) visually examines images on the reflective mirror 11, thereby judging the condition of the targets. Nevertheless, there are some drawbacks during inspection of the nasopharynx, larynx, or mouth cavity using the aforementioned technique. For example, illumination in the nasopharynx, larynx, or mouth cavity is often insufficient. The subject is subject to gag reflex and may require anesthetic during the inspection. Moreover, interaction between the operator (doctor) and the subject (patient) is not practical.

Although a (soft) fiber laparoscope or an (hard) anesthetization laryngoscope can be used to inspect the nasopharynx, larynx, mouth cavity, or nasal cavity of the subject, anesthetization must be utilized therewith, discomforting the subject. Additionally, requirement for high maintenance costs dictates limited applicability of the (soft) fiber laparoscope or (hard) anesthetization laryngoscope in most clinical environments.

U.S. Pat. No. 3,884,222 discloses a laryngoscope transmitting received images via optical fiber. The laryngoscope, however, does not provide illumination of targets.

U.S. Pat. No. 4,915,626 discloses a dental inspection apparatus providing illumination via optical fiber and receiving images using a camera.

U.S. Pat. No. 5,429,502 discloses an electronic video dental camera providing illumination via optical fiber and receiving images using an image sensor.

U.S. Pat. No. 6,050,939 discloses a throat mirror providing illumination via light bulb.

U.S. Pat. No. 6,276,934 discloses a dental camera providing illumination via light source and receiving external images transmitted through a relay lens using a camera head.

BRIEF SUMMARY OF THE INVENTION

A detailed description is given in the following embodiments with reference to the accompanying drawings.

An exemplary embodiment of the invention provides a medical inspection device for inspection of a nasopharynx, a larynx, a mouth cavity, a nasal cavity, an ear passage, and skin, comprising a housing, a reflective layer, a grip, and an optical fiber bundle. The housing comprises a transparent plate and a first opening. The reflective layer is formed in the housing and opposes the transparent plate. The first opening is between the reflective layer and the transparent plate. The grip is connected to the first opening and extends in the exterior of the housing. The optical fiber bundle is connected to the first opening and is disposed in the grip. The optical fiber bundle extends to the exterior of the grip and outputs light into the housing. The light is output to the exterior of the housing by reflection of the reflective layer and through the transparent plate. An image outside the housing is received by the optical fiber bundle through the transparent plate and by reflection of the reflective layer.

The medical inspection device further comprises a reflective mirror disposed in the housing and attached to the transparent plate. The reflective mirror comprises a second opening. The light from the optical fiber bundle is output to the exterior of the housing by reflection of the reflective layer and through the second opening and transparent plate. The image outside the housing is received by the optical fiber bundle through the transparent plate and second opening and by reflection of the reflective layer.

The medical inspection device further comprises a heater and a power line. The heater is connected to the reflective mirror. The power line is connected to the heater and is fit in the grip via the first opening, extending to the exterior of the grip.

The heater comprises a heating coil.

The reflective layer parallels the transparent plate.

The reflective layer parallels the reflective mirror.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
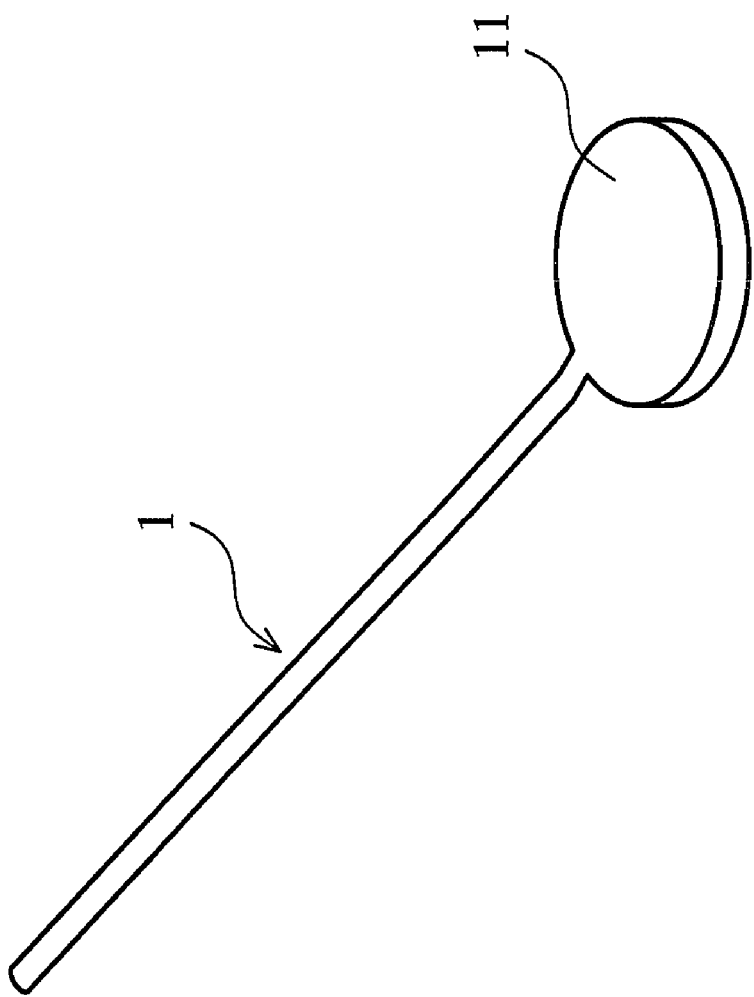
FIG. 1 is a schematic perspective view of a conventional laryngoscope.
Figure 2A:
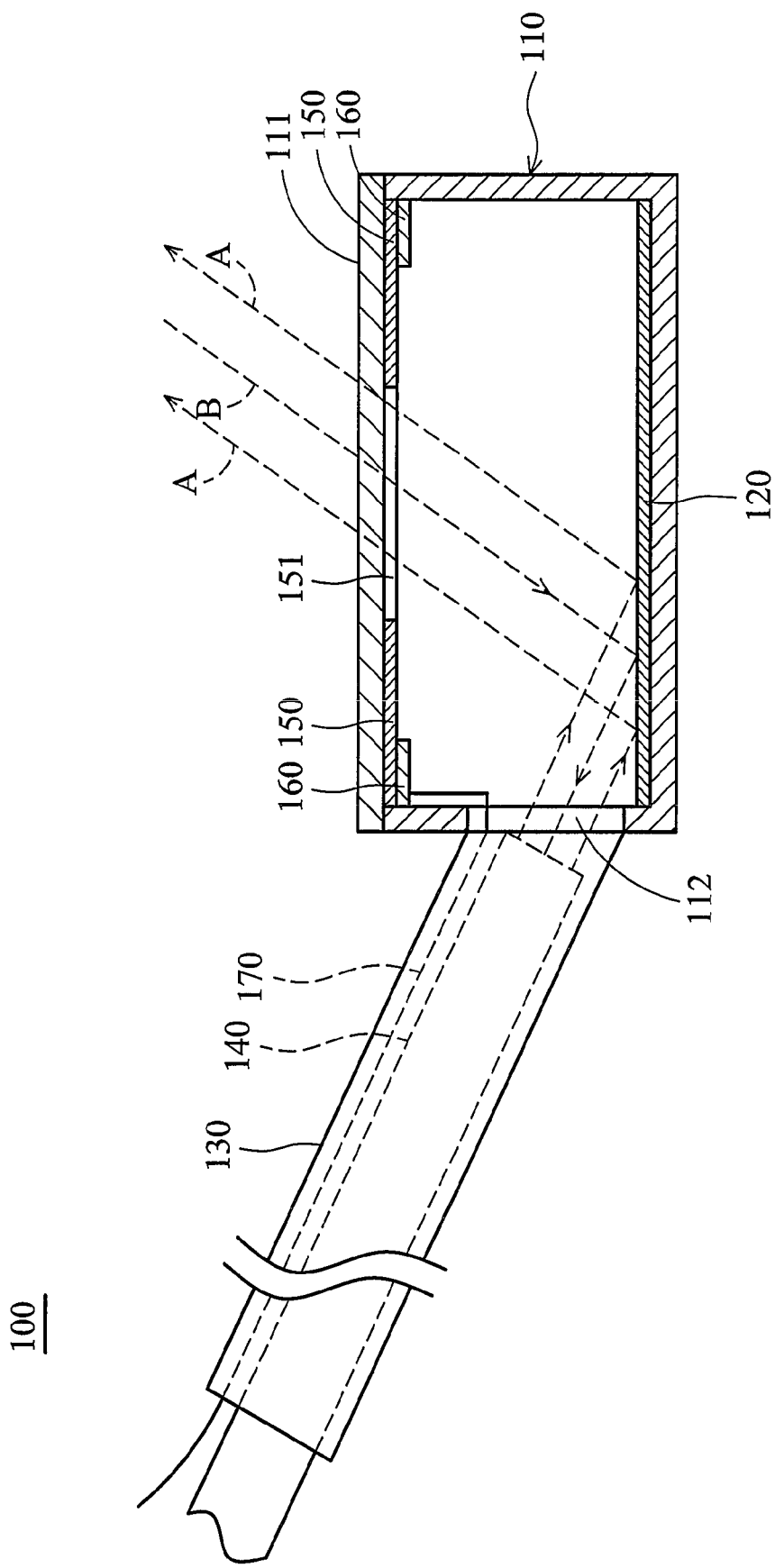
FIG. 2A is a partial cross section and side view of a medical inspection device of an embodiment of the invention.
Figure 2B:
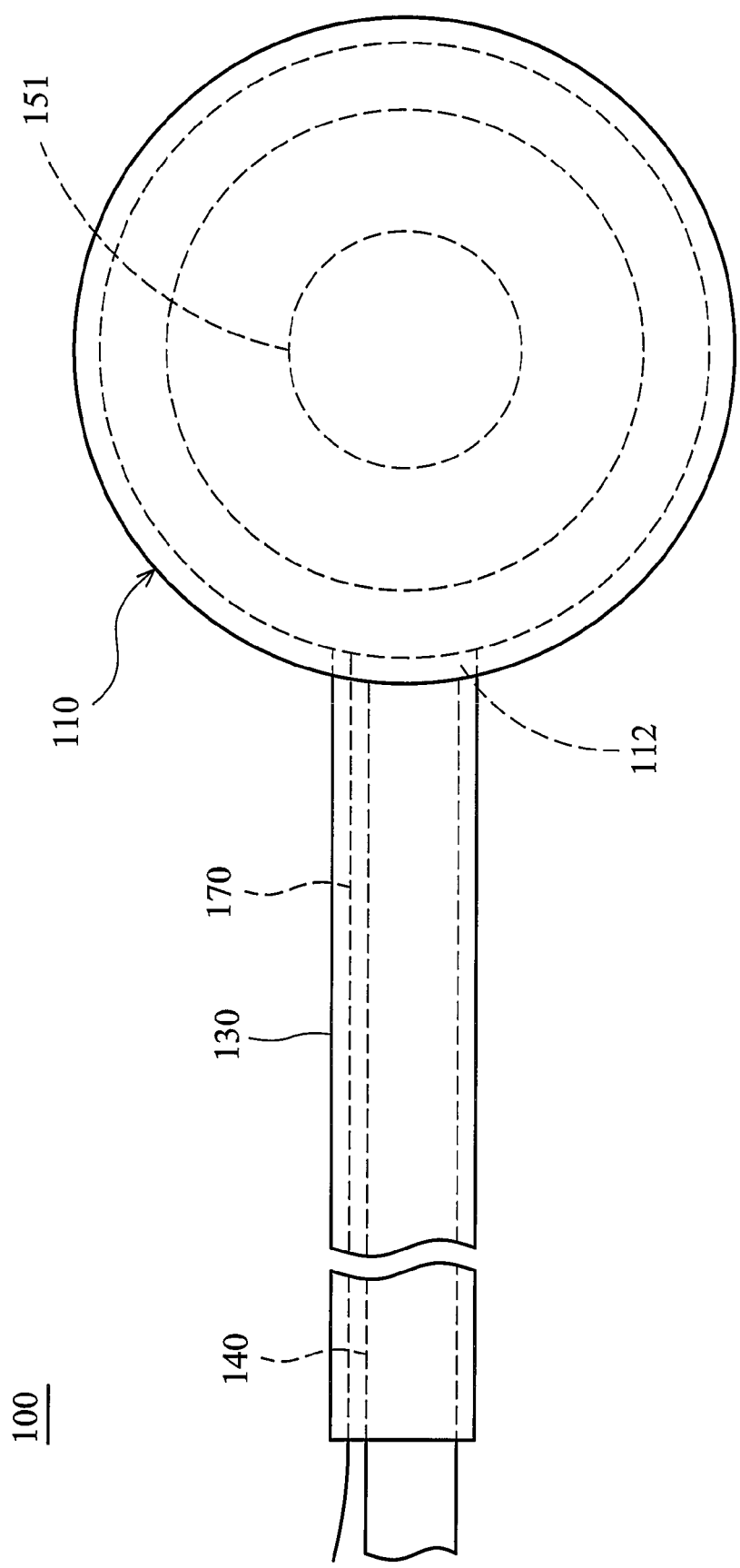
FIG. 2B is a schematic top view of a medical inspection device of an embodiment of the invention.

Referring to FIG. 2A and FIG. 2B, a medical inspection device 100 comprises a housing 110, a reflective layer 120, a grip 130, an optical fiber bundle 140, a reflective mirror 150, a heater 160, and a power line 170.

The housing 110 comprises a transparent plate 111 and a first opening 112.

The reflective layer 120 is formed in the housing 110 and opposes the transparent plate 111. In this embodiment, the first opening 112 is between the reflective layer 120 and the transparent plate 111, and the reflective layer 120 parallels the transparent plate 111, as shown in FIG. 2A. Additionally, the reflective layer 120 may be coated on the bottom of the housing 110 and comprise metal providing light reflection.

The grip 130 is connected to the first opening 112 of the housing 110 and extends in the exterior thereof.

Figure 3:
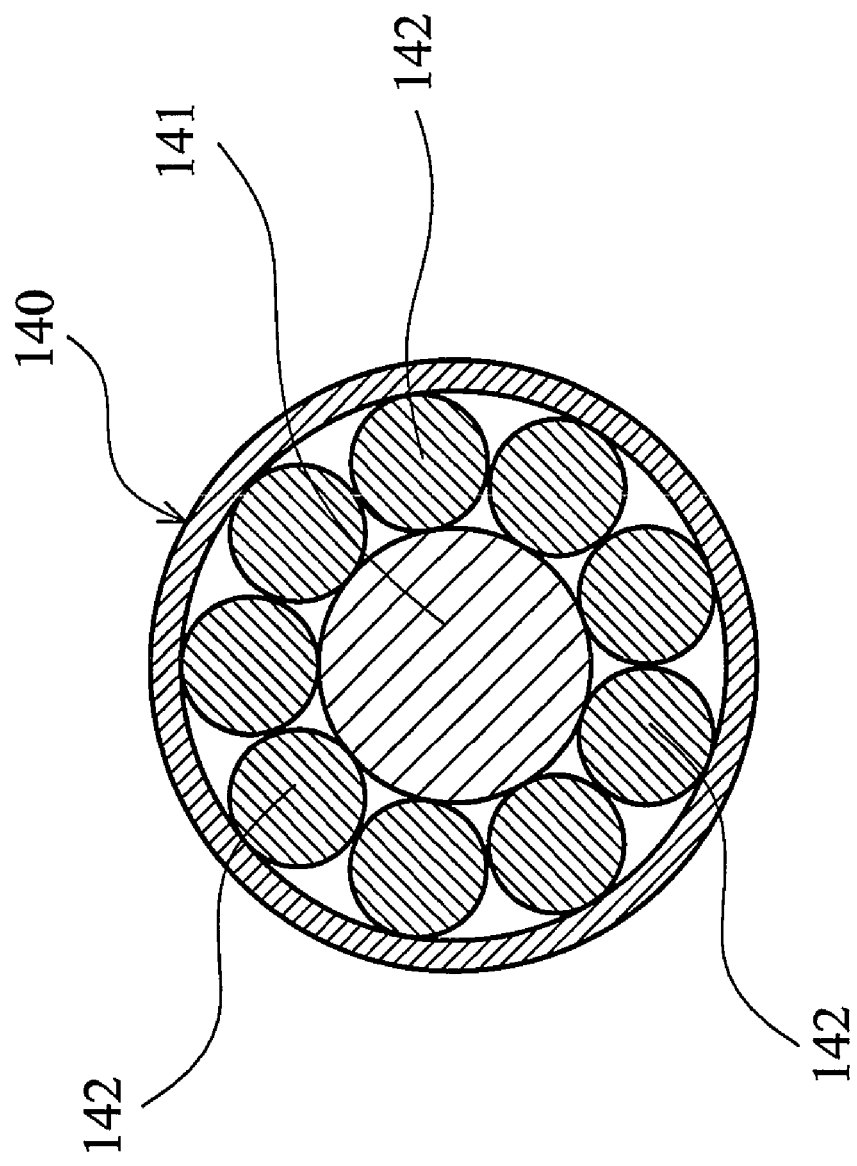
FIG. 3 is a schematic cross section of an optical fiber bundle of a medical inspection device of an embodiment of the invention.

The optical fiber bundle 140 is connected to the first opening 112 of the housing 110 and is disposed in the grip 130. The optical fiber bundle 140 extends to the exterior of the grip 130. A camera (not shown) is connected to the optical fiber bundle 140, receiving images. Moreover, the camera may be connected to a computer (not shown) or a monitor (not shown), via which a subject and an operator can observe images. Specifically, as shown in FIG. 3, the optical fiber bundle 140 comprises a central optical fiber 141 and multiple surrounding optical fibers 142 surrounding the central optical fiber 141. In this embodiment, the central optical fiber 141 receives and transmits images or light (from the interior of the housing 110), and the surrounding optical fibers 142 output light (into the housing 110).

As shown in FIG. 2A, the reflective mirror 150 is disposed in the housing 110 and attached to the transparent plate 111. Specifically, the reflective mirror 150 may be a film coated on the top of the housing 110 and comprising metal providing light reflection. Accordingly, an operator can easily locate a target being inspected by the naked eye, especially for inspection of a nasopharynx or larynx. Moreover, the reflective mirror 150 comprises a second opening 151. In this embodiment, the reflective layer 120 and reflective mirror 150 are parallel to each other and respectively disposed on the top and bottom of the housing 110.

The heater 160 is connected (attached) to the reflective mirror 150. The power line 170 is connected to the heater 160. Here, the heater 160 heats the transparent plate 111 connected to the reflective mirror 150, removing mist produced by breath of a subject. Moreover, the heater 160 may be a heating coil. Specifically, the power line 170 is fit in the grip 130 via the first opening 112 of the housing 110, extending to the exterior of the grip 130 and connected to an external power source (not shown).

When an operator inspects the nasopharynx, larynx, mouth cavity, nasal cavity, or ear passage of a subject using the medical inspection device 100, the surrounding optical fibers 142 of the optical fiber bundle 140 output light, from a rear light box, into the housing 110. The light (as indicated by A in FIG. 2A) is then output to the exterior of the housing 110 by reflection of the reflective layer 120 and through the second opening 151 and transparent plate 111, illuminating the nasopharynx, larynx, mouth cavity, nasal cavity, or ear passage. The operator can initially locate a target by watching the reflective mirror 150 of the medical inspection device 100. When the target is found, an image or light (as indicated by B in FIG. 2A) thereof is received by the central optical fiber 141 of the optical fiber bundle 140 through the transparent plate 111 and second opening 151 and by reflection of the reflective layer 120. The central optical fiber 141 of the optical fiber bundle 140 transmits the image of the target to the monitor. At this point, the operator can easily inspect the magnified target on the monitor and the subject may thereby understand the inspection or even communicate with the operator.

In conclusion, the disclosed medical inspection device is simplified, thus providing reduced manufacturing costs, further suiting common clinical environments. Moreover, the disclosed medical inspection device provides simplified operation, thus reducing inconvenience of inspection.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A medical inspection device, comprising:
    a housing comprising a transparent plate and a first opening;
    a reflective layer formed in the housing and opposing the transparent plate, wherein the first opening is between the reflective layer and the transparent plate;
    a grip connected to the first opening and extending in the exterior of the housing;
    an optical fiber bundle connected to the first opening and disposed in the grip, wherein the optical fiber bundle extends to the exterior of the grip and outputs light into the housing;
    a reflective mirror disposed in the housing and attached to the transparent plate, wherein the reflective mirror comprises a second opening, the light from the optical fiber bundle is output to the exterior of the housing by reflection of the reflective layer and through the second opening and transparent plate, and an image outside the housing is received by the optical fiber bundle through the transparent plate and second opening and by reflection of the reflective layer:
    a heater connected to the reflective mirror; and
    a power line connected to the heater and fit in the grip via the first opening, extending to the exterior of the grip.

2. The medical inspection device as claimed in claim 1, wherein the heater comprises a heating coil.

3. The medical inspection device as claimed in claim 1, wherein the reflective layer parallels the transparent plate.

4. The medical inspection device as claimed in claim 1, wherein the reflective layer parallels the reflective mirror.

* * * * *